United States Patent [19]

DeVitis

[11] 4,332,248
[45] Jun. 1, 1982

[54] MEDICAL APPARATUS

[76] Inventor: Thomas N. DeVitis, 803 Adams Dr., Brookhaven, Pa. 19015

[21] Appl. No.: 174,167

[22] Filed: Jul. 31, 1980

[51] Int. Cl.$^3$ .............................................. A61M 05/00
[52] U.S. Cl. ................................. 128/214 R; 128/133; 128/DIG. 26
[58] Field of Search .................. 128/214 R, 215, 133, 128/DIG. 26, 327

[56] References Cited

U.S. PATENT DOCUMENTS

| | | | |
|---|---|---|---|
| 1,824,516 | 9/1931 | Tyvand | 128/327 |
| 2,008,340 | 7/1935 | Salvati et al. | 128/215 |
| 2,103,174 | 12/1937 | Posada | 128/215 |
| 2,234,961 | 3/1941 | Canada | 128/215 X |
| 2,402,306 | 6/1946 | Turkel | 128/214 R |
| 3,324,854 | 6/1967 | Weese | 128/215 |
| 3,927,660 | 12/1975 | Tegtmeyer | 128/214 R X |
| 4,196,735 | 4/1980 | Ayer | 128/327 |

FOREIGN PATENT DOCUMENTS 1003251 11/1951 France ............................ 128/133

Primary Examiner—Dalton L. Truluck
Attorney, Agent, or Firm—Robert S. Lipton; Robert B. Famiglio; Jack D. Puffer

[57] ABSTRACT

An apparatus or guide to aid in inserting the needle of syringes and the like into body conduits such as veins, is disclosed. The apparatus includes a pair of members which are placed on the opposite sides of a vein, parallel to the longitudinal axis thereof, thereby preventing lateral movement of the vein while it is being pierced by the needle. In an embodiment of the invention a guide is provided to aid in inserting the needle to the desired depth.

4 Claims, 8 Drawing Figures

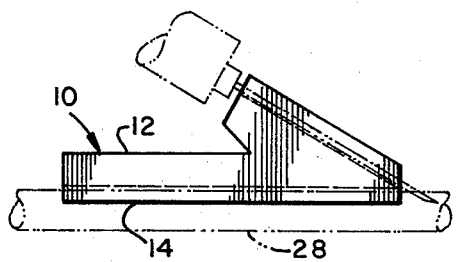 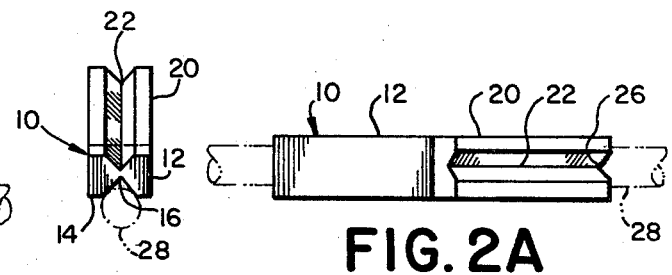
FIG. 1  FIG. 2  FIG. 2A
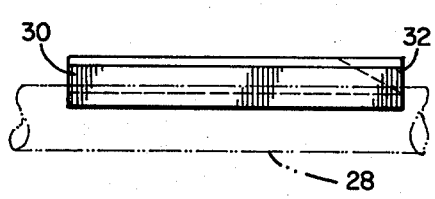 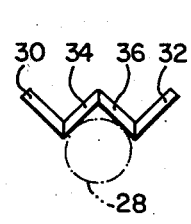 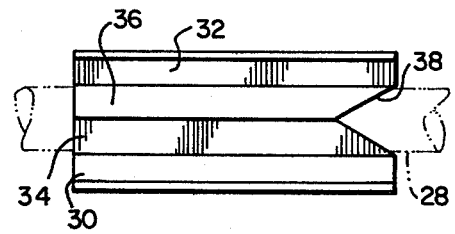
FIG. 3  FIG. 4  FIG. 5
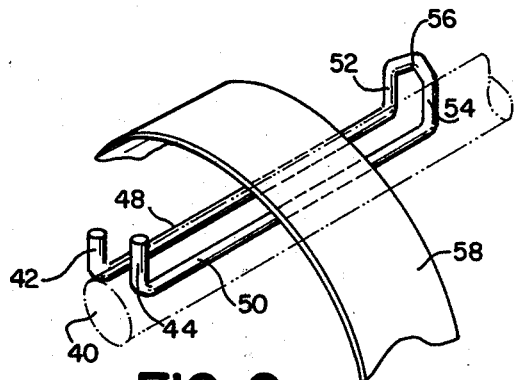
FIG. 6
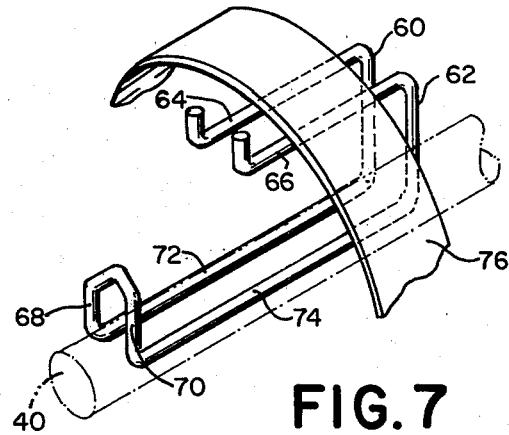
FIG. 7

MEDICAL APPARATUS

BACKGROUND OF THE INVENTION

This invention relates to medical apparatus in general and in particular to medical apparatus useful in aiding medical personnel in locating and stabilizing veins and like physical body conduits when it is necessary to pierce such conduits to inject medication or other substances or to withdraw body fluids from such conduits.

The piercing of body conduits, and in particular, small veins or arteries is a sometimes difficult procedure requiring substantial skill on the part of the operator. Once the vein is located it is difficult to hold it steady while inserting a hollow needle in a specified depth into the vein. If the needle is not perfectly centered on the vein or if the needle is not perfectly pointed towards the vein, the vein will often move laterally with respect to the direction of insertion of the needle as soon as the initial pressure is applied. When this occurs it is necessary to begin the procedure over again, thus, increasing the anxiety of the patient and requiring additional time of the operator.

An additional problem associated with piercing body conduits is controlling the degree of insertion of the needle through the skin and into the body conduit or vein. It is not uncommon for the needle to be inserted to far, thereby causing the passage through the conduit to be missed. This may reduce the effectiveness of the procedure and cause soreness and attendant swelling.

SUMMARY OF THE INVENTION

The present invention overcomes these disadvantages by providing a mechanical means for restraining a body conduit while a needle is inserted so that only a single attempt is required. The invention provides a bifurcated tool which provides lateral support on both sides of a conduit. The bifurcated end of the tool is placed so that one tine is at each side of the vein. By applying light pressure to the tool the vein is restrained in a steady position. Additionally, a guide may be provided to aid in proper degree of insertion of the needle.

The medical apparatus of the instant invention provides a tool having a bifurcated end which is adapted to be place astride a body conduit of an animal to provide steady lateral support when the conduit is to be pierced by a needle for injecting or withdrawing fluids from the conduit. It may be formed from a solid block of material with a V-shaped groove in the lower side thereof which form the required bifurcation. The groove is place directly over the conduit and when light pressure is applied the conduit is restrained in the groove. The device may also be made from sheet material such as metal or plastic formed generally in the shape of a inverted V in cross section and having a V-shaped notch cut in one end with the open end of the V facing the operative end of the tool. In operation, the tool is placed over the conduit such that the V-shaped notch is directly over the conduit and restrains the conduit when light pressure is applied.

Accordingly, it is an object of the present invention to provide an apparatus for preventing lateral movement of body conduits when they are pierced by a needle.

It is another object of the present invention to provide an apparatus for preventing lateral movement of body conduits while they are being pierced by a needle and to provide a guide for aiding the operator to determine the degree of insertion of the needle.

Other further objects and advantages of the invention will become apparent in reviewing the following specification, claims, and drawings in which like numerals refer to like parts.

BRIEF DESCRIPTION OF THE DRAWINGS

FIG. 1 is a side view of one embodiment of the invention.

FIG. 2 is a side view of the embodiment of FIG. 1.

FIG. 2a is a plan view of the embodiment of FIG. 2.

FIG. 3 is a side view of a second embodiment of the invention.

FIG. 4 is an end view of the embodiment of FIG. 3.

FIG. 5 is a plan view of the embodiment of FIG. 3.

FIG. 6 is an isometric view of another embodiment of the present invention.

FIG. 7 is an isometric view of yet another embodiment of the invention.

DESCRIPTION OF THE PREFERRED EMBODIMENT

Referring now to FIGS. 1 and 2 of the accompanying drawings, there is illustrated one embodiment of the invention.

The body of the tool shown generally at 10 is provided with an upper surface 12 and a lower surface 14. In the lower surface 14 there is provided a groove 16 of an inverted V-shaped running generally along the length of the body 10. Projecting from the upper surface 12 is an angularly positioned portion 20. This portion also has a V-shape groove running along the upper surface 18 of the projection 20. This groove is better illustrated in FIG. 2 and is shown at 22. FIG. 2a, a plane view of the embodiment shows the compound V-shape which is formed by the intersection 26 of grooves 16 and 22.

It can be seen that when the lower surface 14 is placed atop and along a body conduit shown in phantom lines at 28, the conduit is restrained from lateral movement. Of course, the body conduit 28 is positioned in body tissue underneath a layer of skin, which is not shown in the drawings in the interest of clarity.

Another feature of this embodiment is provided by the projection 20 described above. The rearward angled surface of the projection 20 provides support for a syringe generally used in injecting or withdrawing fluid from a conduit and can provide a limit stop or guide to insure proper degree of insertion of the needle. In addition, the inclined groove 22 gives directional guidance and support for the needle.

Referring now to FIGS. 3, 4 and 5 there is illustrated a second embodiment of the invention.

This embodiment, shown in elevation in FIG. 3 is made of sheet material such as metal or plastic. This embodiment is formed in a generally W-shape as shown in FIG. 4.

The outer legs of the W shown at 30 and 32 form the exterior surfaces of the device. The inner legs 34 and 36 form an inverted V-shape on the upper side of the device. There is formed at one end of the device a V-shaped notch 38 placed in a longitudinal orientation.

The operation of this embodiment is essentially the same as that described in connection with FIG. 1 above. The open end of the W-shape is placed atop and along a conduit shown in phantom at 40. As gentle pressure is applied downward, the conduit is restrained in the notch 38.

Referring now to FIG. 6, there is shown yet another embodiment of the invention. This embodiment is formed of a single piece of rod-like material such as a metallic wire or molded plastic or the like. As in the previous embodiments, a pair of separated surfaces are provided by the two arms 42 and 44. These arms are separated so as to be placed on either side of a conduit as shown at 40. Formed continuously with the arms 42 and 44 are two longitudinal members 48 and 50 which lie along the conduit's longitudinal axis. The longitudinal members 48 and 50 terminate in a second upright portion formed by vertical arms 52 and 54 which are joined by an inverted V member 56.

The operation of this embodiment is similar to that described with reference to the embodiments shown in FIGS. 1 through 5. This embodiment shows the device being retained over the conduit using a retaining means. The vertical portions formed by the pairs of vertical arms 42, 44, 52 and 54 provide end walls at the end of the longitudinal members 48 and 50 which will hold a binding member 58 over the device. This binding member may be, for example, a length of tape wrapped around the body member containing the conduit. With this embodiment the device may be held securely while a needle is withdrawn or inserted into the conduit. It is to be noted that the embodiment shown in FIGS. 1 through 5 have similar retaining means which are adapted for identical use but are not so shown in the interest of clarity.

Referring now to FIG. 7 there is shown another embodiment of the invention similar to that described in connection with FIG. 6 above. This embodiment differs from the embodiment of FIG. 6 in that the vertical arms 60 and 62 are substantially longer than the vertical arms 52 and 54 of FIG. 6. At the upper ends of arms 60 and 62 there is provided a second pair of longitudinal members 64 and 66. These longitudinal members are substantially parallel to the longitudinal members 72 and 74 which are placed along the conduit. These second longitudinal members terminate in vertical portions 68 and 70. Between the vertical portions 68 and 70 an inverted V connecting member 71 similar to 56 is described in connection with FIG. 6 above. Over the longitudinal members 64 and 66 between the vertical portions there is placed a retaining member 76 which is used to secure the device over the axis of the conduit.

While specific embodiments of the invention have been illustrated and described, it is to be understood that these embodiments are provided by way of example only and that the invention is not to be construed as being limited thereto, but only by the proper scope of the following claims.

What is claimed is:

1. A device for laterally restraining a fluid conduit comprising:
   first and second legs spaced apart from each other; and
   body means having a longitudinal axis and connecting said legs at a distance from their distal ends, said body means including:
   a space along its longitudinal axis for receiving a fluid conduit therein;
   upper and lower horizontal surface parallel to each other and to the longitudinal axis of said body means;
   a third surface inclined to the axis of said body means and connecting the upper and lower surfaces of said body means, said inclined surface having a V-shaped groove formed therein, said groove terminating in said first and second legs; and
   a second inclined surface orthogonal to said first inclined surface and connecting said first inclined surface with the upper surface of said body means.

2. A device for laterally restraining a fluid conduit comprising:
   first and second legs spaced apart from each other; and
   body means having a longitudinal axis and connecting said legs at a distance from their distal ends, said body means having a space along its longitudinal axis for receiving fluid conduit therein, said body being formed of a unitary member having first and second vertical members forming said first and second legs and third and fourth vertical members connected by a horizontal member; and first and second lateral members respectively connecting first and second vertical members to each other and said third and second vertical members to each other.

3. The device according to claim 1 and further comprising third and fourth longitudinal members respectively attached to said third and fourth vertical members and extending parallel to said first and second longitudinal members and spaced vertically apart therefrom, said third and fourth longitudinal members terminating approximately over said first and second vertical members.

4. The device according to claim 3 wherein said third and fourth longitudinal members terminate in fifth and sixth vertical members extending upward from said first and second vertical members.

* * * * *